(12) United States Patent
Makino et al.

(10) Patent No.: US 9,506,942 B2
(45) Date of Patent: Nov. 29, 2016

(54) AUTOMATIC ANALYZER AND METHOD FOR DETECTING MEASUREMENT VALUE ABNORMALITIES

(71) Applicant: HITACHI HIGH-TECHNOLOGIES CORPORATION, Tokyo (JP)

(72) Inventors: Akihisa Makino, Tokyo (JP); Masahiko Iijima, Tokyo (JP); Akiko Watanabe, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/367,066

(22) PCT Filed: Nov. 22, 2012

(86) PCT No.: PCT/JP2012/080377
§ 371 (c)(1),
(2) Date: Jun. 19, 2014

(87) PCT Pub. No.: WO2013/099486
PCT Pub. Date: Jul. 4, 2013

(65) Prior Publication Data
US 2014/0356964 A1 Dec. 4, 2014

(30) Foreign Application Priority Data
Dec. 26, 2011 (JP) .................................. 2011-284467

(51) Int. Cl.
*G01N 35/10* (2006.01)
*G01N 35/00* (2006.01)
G01N 21/53 (2006.01)

(52) U.S. Cl.
CPC .... *G01N 35/1002* (2013.01); *G01N 35/00663* (2013.01); *G01N 35/00693* (2013.01); G01N 21/532 (2013.01); G01N 35/00603 (2013.01); G01N 2035/00702 (2013.01); Y10T 436/11 (2015.01)

(58) Field of Classification Search
CPC .. G01N 35/1002; G01N 35/10; G01N 35/00; G01N 35/00663; G01N 35/00631; G01N 35/00594; G01N 35/00584; Y10T 436/11; Y10T 436/00
USPC .......................... 436/43; 422/82.05, 68.1, 50
See application file for complete search history.

(56) References Cited

U.S. PATENT DOCUMENTS 4,234,538 A * 11/1980 Ginsberg ............. G01N 21/253
250/226
4,762,413 A * 8/1988 Namba ................ G01N 21/253
250/574
2001/0006819 A1 7/2001 Kawamura
2009/0222213 A1 9/2009 Hamazumi et al.
2011/0110822 A1* 5/2011 Adachi ................ G01N 21/253
422/82.09
2012/0020838 A1* 1/2012 Mimura et al. .................. 422/73
2012/0288409 A1 11/2012 Inabe et al.
2013/0108509 A1* 5/2013 Shiba et al. ............... 422/82.05
2013/0132022 A1 5/2013 Tamura et al.

FOREIGN PATENT DOCUMENTS

| CN | 101339198 A | 1/2009 | |
|---|---|---|---|
| EP | 2562547 A1 | 2/2013 | |
| EP | 2587250 A1 | 5/2013 | |
| EP | 2587251 A1 | 5/2013 | |
| EP | 2866022 A1 | 4/2015 | |
| JP | 06-7054 U | 1/1994 | |
| JP | 2000-275254 A | 10/2000 | |
| JP | 2001-249134 A | 9/2001 | |
| JP | 2004-347385 A | 12/2004 | |
| JP | 2006-337125 A | 12/2006 | |
| JP | 2007-248089 A | 9/2007 | |
| JP | 2007-322324 A | 12/2007 | |
| JP | 2010-141430 * | 6/2010 | ............. G01N 33/86 |
| JP | 2011-013142 A | 1/2011 | |
| JP | 2011-153944 A | 8/2011 | |
| JP | 2011-174842 A | 9/2011 | |
| JP | 2012-141246 A | 7/2012 | |

(Continued)

OTHER PUBLICATIONS

International Preliminary Report on Patentability received in International Application No. PCT/JP2012/080377 dated Jul. 10, 2014.
Chinese Office Action received in corresponding Chinese Application No. 201280064619.8 dated Dec. 31, 2014.
Chinese Office Action received in corresponding Chinese Application No. 201280064619.8 dated Jul. 21, 2015.
Japanese Office Action received in corresponding Japanese Application No. 2011-284467 dated Nov. 10, 2015.

(Continued)

*Primary Examiner* — Christine T Mui
(74) *Attorney, Agent, or Firm* — Mattingly & Malur, PC

(57) ABSTRACT

An automatic analyzer detects measurement value abnormalities stemming from reaction process anomalies caused by the presence of foreign matter or bubbles. It is determined whether the results of concentration calculation based on light quantity data from multiple target detectors each fall within an applicable determination range. If the results fall within the determination range, an average value of the results of concentration calculation with the target detectors is calculated, and if not, an out-of-determination-range flag is given. A default fluctuation range is retrieved regarding the average value of the results of concentration calculation. The fluctuation range of the results of concentration calculation with the multiple target detectors is calculated. If the fluctuation range is found to fall within the default range, the results of concentration calculation are output to a display; and if outside the default range, a reexamination request is displayed with an added measurement value abnormality alarm.

13 Claims, 7 Drawing Sheets

(56) References Cited

FOREIGN PATENT DOCUMENTS

| | | | |
|---|---|---|---|
| JP | 2012-149903 A | 8/2012 | |
| JP | 2014-21008 A | 2/2014 | |
| WO | WO 2010/0117044 | * 10/2010 | ............ G01N 33/04 |
| WO | 2011/093402 A1 | 8/2011 | |
| WO | 2011/132525 A1 | 10/2011 | |
| WO | 2011/162113 A1 | 12/2011 | |
| WO | 2011/162139 A1 | 12/2011 | |

OTHER PUBLICATIONS

Keller, H. et al., "Performance Profiles: New Tools for Characterization and Comparison of Clinical Chemical Results", J. Clin. Chem. Clin. Biochem., 1989, pp. 613-629, vol. 27, Berlin, New York.

Extended European Search Report received in corresponding European Application No. 12861407.0 dated Jul. 21, 2015.

* cited by examiner (1) SUDDEN FLUCTUATION AT SINGLE POINT OF MEASUREMENT

BUBBLES, FOREIGN MATTER (2) SUDDEN FLUCTUATIONS AT MULTIPLE POINTS OF MEASUREMENT

SETTLING

BUBBLES, FOREIGN MATTER (3) GRADUAL FLUCTUATIONS THROUGHOUT THE ENTIRE REACTION PROCESS

BUBBLES

| ITEM NAME | ABC | | | |
|---|---|---|---|---|
| UNIT | | CONCENTRATION RANGE | | ACCEPTABLE FLUCTUATION RANGE |
| mg/dL | 0.01 | — | 0.1 | 0.01 |
| | | — | 1.0 | 0.1 |
| | | — | 5.0 | 1.0 |
| | | — | 50.0 | 2.0 |
| | | — | | |

AUTOMATIC ANALYZER AND METHOD FOR DETECTING MEASUREMENT VALUE ABNORMALITIES

TECHNICAL FIELD

The present invention relates to an automatic analyzer for analyzing the quantities of ingredients in samples such as blood and urine.

BACKGROUND ART

Automatic analyzers are used extensively to analyze the quantity of an ingredient in a sample, the analyzers applying light from a light source to the sample or to a reaction mixture that mixes the sample with a reagent, measuring the volume of resulting transmitted light of a single or multiple wavelengths, and calculating absorbance accordingly to determine the quantity of the ingredient. The quantity of the ingredient is calculated in accordance with the Lambert-Beer law.

With the above type of automatic analyzer, numerous reaction cells holding the reaction mixture are arranged circumferentially on a reaction disk that rotates and stops repeatedly. While the reaction disk is being rotated, a prearranged transmitted light measurement unit measures chronological changes in the absorbance at predetermined time intervals for about 10 minutes. Upon completion of the measurement, the reaction cells are washed by a washing mechanism before being used for another analysis.

Two major kinds of analyses are employed: color reactions involving substrates and enzymes, and agglutination reactions involving antigens and antibodies. The former kind of analyses represents biochemical analyses of which the test items include LDH (lactate dehydrogenase), ALP (alkaline phosphatase), and AST (aspartate aminotransferase). The latter kind of analyses denotes immunoassays of which the test items include CRP (C-reactive protein), IgG (immunoglobulin), and RF (rheumatoid factor).

A highly sensitive detection system is required for the above-mentioned immunoassays because the substances to be measured thereby have low blood concentrations. For example, consider the case where a reagent of latex particles whose surface is sensitized (bonded) with antibodies is used in an antigen-antibody reaction with antigens contained in a sample so as to bring about the agglutination of latex aggregates. In this case, light is applied to the reaction mixture, and the quantity of transmitted light (i.e., light not scattered by the latex aggregates) is measured to determine the quantity of an ingredient in the sample by what is known as the latex coagulating method for highly sensitive measurement.

Further, attempts have been made with automatic analyzers to measure the quantity of not transmitted light but scattered light from the sample for highly sensitive measurement.

Meanwhile, with the above-described automatic analyzers, there have been cases where the light from the light source is partially blocked or scattered by the presence of foreign matter or bubbles inside the reaction cells or within a fluid in a thermostatic bath outside the reaction cells, causing abnormalities in the reaction process that determines the quantity of the target substance.

The abnormalities induced by foreign matter or by bubbles in the reaction process may be of three types: (1) a sudden fluctuation at a single point of measurement, (2) sudden fluctuations at multiple points of measurement, and (3) gradual fluctuations throughout the entire reaction process. The abnormality of type (1) above in the reaction process occurs because the foreign matter or bubbles within the fluid inside the thermostatic oven outside the reaction cells traverse the optical axis for photometry, causing a temporary drop in the quantity of transmitted light (rise in absorbance) or a temporary rise in the quantity of scattered light.

The abnormality of type (2) above in the reaction process takes place because the foreign matter or bubbles floating in the reaction mixture in the reaction cells traverse over time the optical axis for photometry, triggering drops in the quantity of transmitted light or rises in the quantity of scattered light at multiple points of measurement.

The abnormality of type (3) above in the reaction process occurs because very small bubbles stuck on the inner wall surface of the reaction cells gradually grow or migrate within a reaction time, causing the measuring luminous flux to be partially blocked or scattered and bringing about a gradual decrease in the quantity of light (gradual increase in absorbance) or a gradual increase in the quantity of scattered light from an apparent reaction taking place.

The above abnormalities in the reaction process are known to affect the correctness or the accuracy of the results of measurement, and constitute a major impediment to bringing about highly sensitive measurement.

The abnormalities of types (1) and (2) in the reaction process can be checked by techniques described in Patent Document 1 for comparing rates of changes in the reaction process or by techniques disclosed in Patent Document 2 for calculating the Mahalanobis distance regarding normal reactions so as to distinguish abnormal reactions.

The abnormality of type (3) above in the reaction process is not easy to check during ordinary inspection work where the concentration of the target substance is unknown, because the reaction process is apparently normal.

Given the circumstances, Patent Document 3 discloses techniques involving an image acquisition unit for directly imaging the reaction cells in addition to the measurement unit for measuring the absorbance of the reaction mixture, whereby the reaction process and image information are used to check reaction process abnormalities caused by bubbles or the like.

PRIOR ART DOCUMENTS

Patent Documents

Patent Document 1: JP-2000-275254-A
Patent Document 2: JP-2007-248089-A
Patent Document 3: JP-2011-013142-A

SUMMARY OF THE INVENTION

Problem to be Solved by the Invention

However, with the techniques described in Patent Document 3, it is impossible to determine on which part of the inner walls of the reaction cells the bubbles are going to be stuck. This requires imaging multiple locations on the inner walls, which complicates the mechanisms of imaging equipment.

Where scattered light is measured with high sensitivity, the measurement may conceivably be affected by the presence of bubbles several $\mu m$ in diameter. To check such infinitesimal bubbles requires imaging at high resolution and poses the problems of processing speed and recording capacity, among others.

Furthermore, even if the reaction process and the acquired images are checked at the same time, it is difficult to determine to what extent the results of measurement have been actually affected. As a result, even if the effects on the results of measurement are small enough to be negligible, it may be determined that reexamination is necessary, which can lead to the wasteful use of reagents. In particular, the effects on the results of measurement are difficult to determine in the case of gradual fluctuations throughout the entire reaction process as in the abnormality of type (3) above.

An object of the present invention is to realize an automatic analyzer and a method for detecting measurement value abnormalities stemming from reaction process anomalies caused by the presence of foreign matter or bubbles without recourse to complicated processing or functionality of the analyzer.

Means for Solving the Problem

In order to achieve the above object, the present invention is constituted as follows:

There is provided an automatic analyzer for analyzing a sample as well as a method for detecting measurement value abnormalities, the automatic analyzer including a sample pipetting mechanism for pipetting the sample into reaction cells, a plurality of light intensity detectors, and a display unit for displaying the result of analyzing the sample. Multiple detection values from the multiple light intensity detectors detecting the same sample are used to calculate the concentration of the sample, and a fluctuation range of the calculated concentrations is obtained. It is then determined whether the calculated fluctuation range falls within a predetermined acceptable fluctuation range. If the concentration calculated from any one of the detection values from any one of the multiple light intensity detectors does not fall within the acceptable fluctuation range, the display unit is caused to indicate that a reaction process abnormality has occurred.

Effects of the Invention

It is thus possible to implement an automatic analyzer and a method for detecting detection value abnormalities stemming from reaction process anomalies caused by bubbles or foreign matter without recourse to complicated processing or functionality of the analyzer.

MODES FOR CARRYING OUT THE INVENTION

Figure 1:
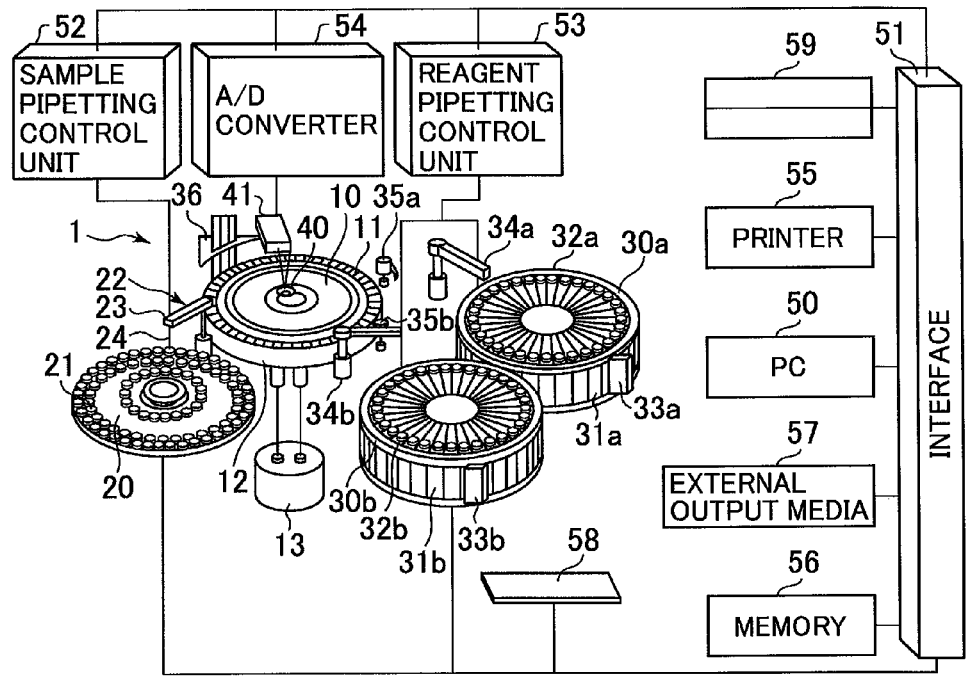
FIG. 1 is an overall configuration diagram of an automatic analyzer to which one embodiment of the present invention is applied.

One embodiment of the present invention will now be described in detail with reference to the accompanying drawings.

In explaining the embodiment of the invention, all entities having the same functions will be designated by the same reference characters throughout the drawings, and their descriptions will be omitted where redundant.

Embodiment

FIG. 1 is an overall configuration diagram of an automatic analyzer to which one embodiment of the present invention is applied. In FIG. 1, the automatic analyzer 1 is furnished mainly with a reaction disk (reaction cell storage mechanism) 10, a sample disk 20, reagent disks (reagent container storage mechanisms) 30a and 30b, a light source 40, a photometer 41, and a computer 50.

The reaction disk 10 can be rotated intermittently. Numerous reaction cells 11 made of a transparent material are arranged circumferentially on the reaction disk 10. The reaction cells 11 are maintained at a constant temperature (e.g., 37° C.) by a thermostatic bath 12. A fluid inside the thermostatic bath 12 is temperature-controlled by a constant temperature unit 13.

On the sample disk 20, numerous sample containers 21 holding a biological sample such as blood or urine are arranged in two circumferential arrays in the illustrated example. Near the sample disk 20 is a sample pipetting mechanism 22. The sample pipetting mechanism 22 is equipped with a movable arm 23 and a pipette nozzle 24 attached to the mechanism 22.

In the above configuration, the sample pipetting mechanism 22 has the pipette nozzle 24 moved to a pipetting position by the movable arm 23 at sample pipetting time, aspirating a predetermined amount of the sample from inside the sample container 21 positioned at an aspirating position of the sample disk 20 and discharging the aspirated sample into the reaction cell 11 at a discharging position on the reaction disk 10.

The reagent disks 30a and 30b are approximately the same in diameter and have about the same shape. Reagent cooling boxes 31a and 31b are arranged circumferentially on the reagent disks 31a and 30b respectively. In the reagent cooling boxes 31a and 31b, multiple reagent bottles 32a and 32b each bearing a label indicating reagent identification information such as a barcode are placed on the reagent disks 30a and 30b in the circumferential arrays.

These reagent bottles 32a and 32b contain a reagent solution corresponding to the analysis items that can be analyzed by the automatic analyzer 1. Also, the reagent cooling boxes 31a and 31b are furnished with barcode readers 33a and 33b respectively. At reagent registration time, the barcode readers 33a and 33b read the barcodes indicated on the outer walls of the reagent bottles 32a and 32b. The reagent information thus read is registered in a memory 56 together with the positions on the reagent disks 30a and 30b.

Near the reagent disks 30a and 30b are reagent pipetting mechanisms 34a and 34b, respectively, which are approximately the same mechanically as the sample pipetting mechanism 22. At reagent pipetting time, the pipette nozzles of the mechanisms 34a and 34b aspirate the reagent solution corresponding to the test items of interest from inside the reagent bottles 32a and 32b positioned at reagent receiving positions on the reaction disk 10, the aspirated reagent solution being discharged into the relevant reaction cells 11.

Stirring mechanisms 35a and 35b are located surrounded by the reaction disk 10, reagent disks 30a and 30b, and reagent pipetting mechanisms 34a and 34b. The reaction of a liquid mixture of the sample and reagent in the reaction cells 11 is promoted when the mixture is stirred by the stirring mechanisms 35a and 35b.

Here, the light source 40 is located near the center of the reaction disk 10, and the photometer 41 is positioned at the outer circumference of the reaction disk 10. The row of the reaction cells 11 having been stirred is rotated in a manner passing a photometry position flanked by the light source 40 and the photometer 41. Incidentally, the light source 40 and the light scattering photometer 41 constitute an optical detection system.

The reaction mixture of the sample and reagent in each reaction cell 11 is measured photometrically every time it passes in front of the photometer 41 while the reaction disk 10 is being rotated. An analog signal of the scattered light measured per sample is input to an A/D (analog/digital) converter 54.

A reaction cell washing mechanism 36 located near the reaction disk 10 washes the inside of the used reaction cells 11 for repeated use.

Figure 2:
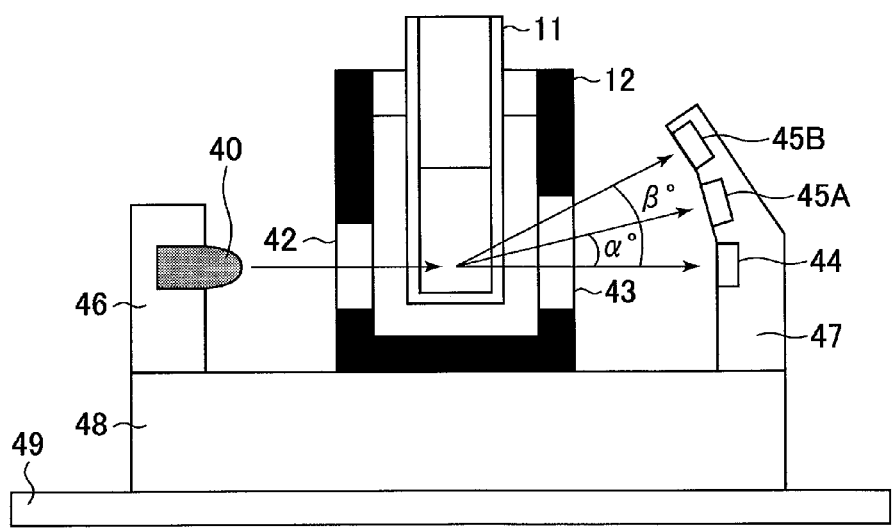
FIG. 2 is a schematic diagram of an optical system in the embodiment of the present invention.

Next, a control system and a signal processing system of the automatic analyzer 1 in FIG. 2 are explained briefly. The computer 50 is connected via an interface 51 to a sample pipetting control unit 52, a reagent pipetting control unit 53, and the A/D converter 54. The computer 50 sends commands to the sample pipetting control unit 52 to control the sample pipetting operation. Also, the computer 50 transmits commands to the reagent pipetting control unit 53 to control the reagent pipetting operation.

Photometric values output from the photometer 41 and converted to digital signals by the A/D converter 54 are input to the computer 50.

The interface 51 is connected with a printer 55 for printing, a memory 56 and external output media 57 serving as storage devices, a keyboard for inputting operation commands and the like, and a CRT display (display device) 59 for screen display. In place of the CRT display, a liquid crystal display or some other display may be adopted as the display device 59.

The memory 56 may be composed of a hard disk memory or an external memory, for example. The memory 56 stores such information as the password of each operator, display levels of different screens, application parameters, details of requested analysis items, results of calibration, and results of analyses.

Next, the sample analyzing operation performed by the automatic analyzer 1 in FIG. 1 is explained. The application parameters regarding the items that can be analyzed by the automatic analyzer 1 are assumed to have been input beforehand via an information input device such as the keyboard 58 and stored in the memory 56. An operator selects the test items requested of each sample using an operation function screen on the display 59.

At this point, information such as a patient ID is also input from the keyboard 58. In order to analyze the test items designated for each sample, the pipette nozzle 24 of the sample pipetting mechanism 22 pipettes a predetermined amount of the sample from the sample cell 21 to a reaction cell 11 in accordance with the application parameters.

The reaction cell 11 in which the sample (specimen) has been pipetted is transferred by the rotating reaction disk 10 to the reagent receiving position and stopped. In keeping with the application parameters of the applicable test items, the pipette nozzles of the reagent pipetting mechanisms 34a and 34b pipette a predetermined amount of the reagent into the reaction cell 11. The sample may be pipetted before the reagent as in this example, or vice versa.

Later, the stirring mechanisms 35a and 35b stir the sample and reagent for mixture. When this reaction cell 11 traverses the photometry position, the photometer 41 measures photometrically the transmitted or scattered light from the reaction mixture. The photometrically measured transmitted light or scattered light is converted by the A/D converter 54 to a numerical value proportionate to the quantity of light before being input to the computer 50 via the interface 51.

The numerical values from the conversion are used to calculate concentration data based on the calibration curves measured beforehand by an analysis method designated for each test item. Ingredient concentration data resulting from the analysis of each test item is output to the printer 55 or onto the screen of the CRT display 59.

Before the execution of the above-described measuring operation, the operator registers various parameters and samples necessary for analysis and measurement via an operation screen on the CRT display 59. Also, the operator verifies the results of analyses after measurement using the operation screen on the CRT display 59.

FIG. 2 is a schematic diagram of an optical system in the embodiment of the present invention. In FIG. 2, the light emitted from the light source 40 passes through a light projecting window 42 formed on the thermostatic bath 12 and illuminates the substance targeted for measurement inside the reaction cell 11. The transmitted light from the measurement target substance passes through a light receiving window 43 and is received by a transmitted light detector 44 of the photometer 41. The scattered light from the measurement target substance passes through the light receiving window 43 and is received by scattered light detectors 45a and 45b at angles of $\alpha°$ and $\beta°$, respectively, relative to the optical axis in the photometer 41.

Alternatively, the multiple scattered light detectors may be arranged in a vertically symmetrical manner at the same angle relative to the optical axis. The light source 40 is secured by a light source holder (base component to which the light source is attached) 46. The detectors 44, 45a and 45b of the photometer 41 are placed in and secured by a detector holder (base component to which the detectors are attached) 47.

Also, the light source holder 46 and the detector holder 47 are fixed to a photometer base 48 which in turn is fixed to a mechanism base 49.

Figure 3:
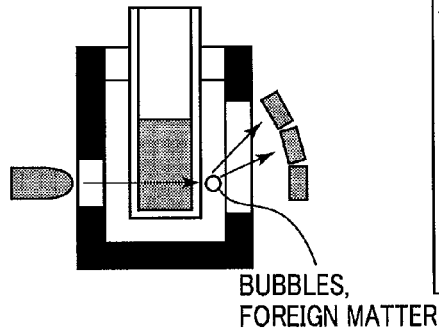
FIG. 3 is an explanatory diagram explaining a sudden fluctuation at a single point of measurement.
Figure 3:
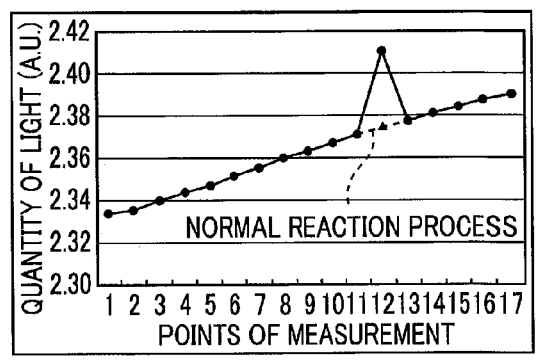
Figure 4:
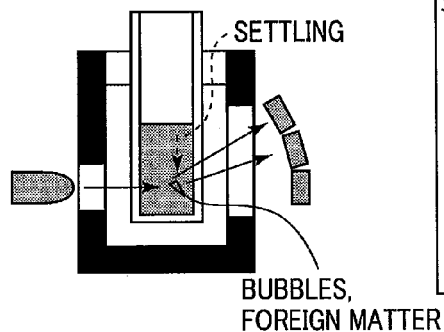
FIG. 4 is an explanatory diagram explaining sudden fluctuations at multiple points of measurement.
Figure 4:
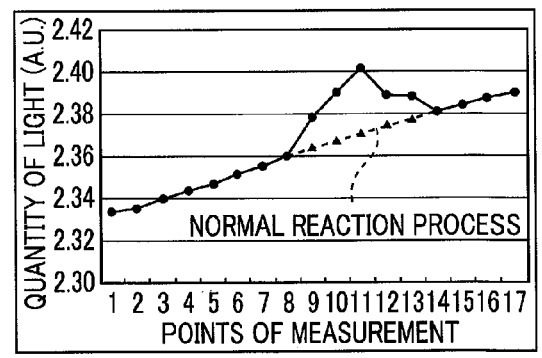
Figure 5:
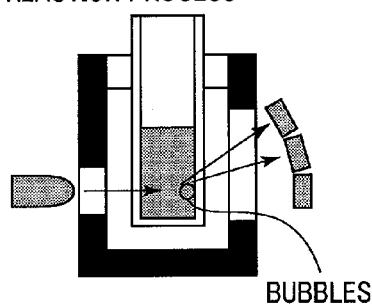
FIG. 5 is an explanatory diagram explaining gradual fluctuations throughout the entire reaction process.
Figure 5:
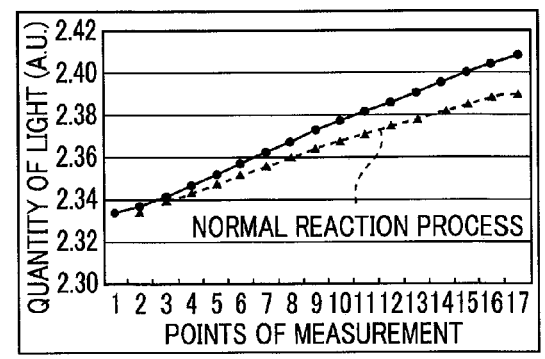

FIGS. 3, 4 and 5 are explanatory diagrams explaining reaction process anomalies caused by bubbles or foreign matter.

FIG. 3 is an explanatory diagram explaining a sudden fluctuation (1) at a single point of measurement. In FIG. 3, the fluctuation occurs because foreign matter or bubbles in the fluid inside the thermostatic bath outside the reaction cell traverse the optical axis for photometry, causing a temporary drop in the quantity of transmitted light (a rise in absorbance) or a temporary rise in the quantity of scattered light.

FIG. 4 is an explanatory diagram explaining sudden fluctuations (2) at multiple points of measurement. In FIG. 4, the fluctuations take place because foreign matter or bubbles floating in the reaction mixture inside the reaction cell traverse over time the optical axis, causing drops in the quantities of transmitted light (rises in absorbance) or rises in the quantities of scattered light at multiple points of measurement.

FIG. 5 is an explanatory diagram explaining gradual fluctuations throughout the entire reaction process. In FIG. 5, the gradual fluctuations throughout the reaction process occur because very small bubbles attached to the wall surface inside the reaction cell gradually grow or migrate during the reaction time, blocking or scattering part of the luminous flux to cause a gradual decrease in the quantity of light (gradual increase in absorbance) or a gradual increase in the quantity of scattered light in an apparent reaction.

If such reaction process anomalies occur at the points of measurement for concentration calculation by the end point assay or the rate assay generally used as the method of analysis with the automatic analyzer, the concentrations resulting from the calculation can be abnormal and lead to abnormal reports.

Figure 6:
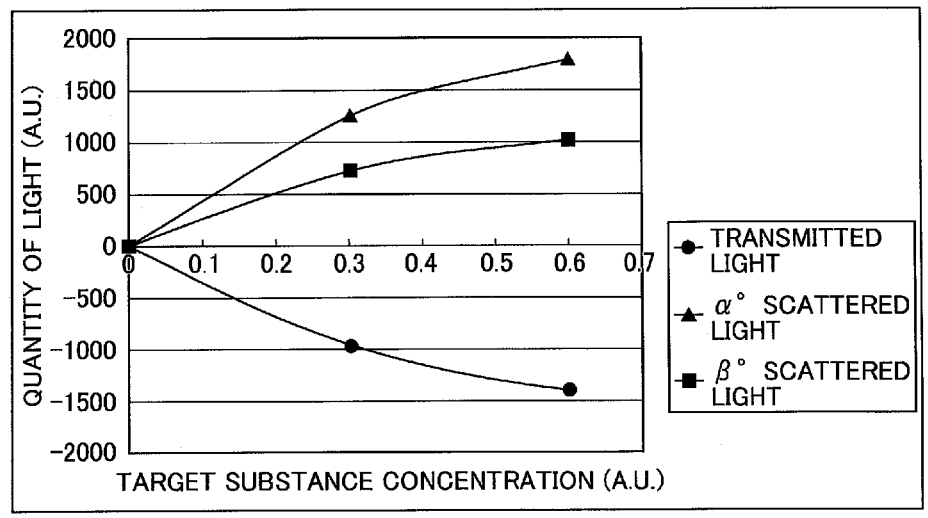
FIG. 6 is a graph showing typical calibration curves of detectors dealing with their respective target substances.

FIG. 6 is a graph showing typical calibration curves of the detectors 44, 45A and 45B dealing with their respective target substances in the embodiment of the present invention. The graph in FIG. 6 shows the case in which standard solutions having graduated concentrations are measured a number of times and the measured quantities of light are averaged to obtain light quantity data at each of the different concentrations whereby the calibration curves are created. Because samples of known concentrations are measured a number of times in creating the calibration curves, it is easy to detect measurement value abnormalities stemming from reaction process anomalies. For this reason, there is no problem even if the means of the present invention are not employed. The calibration curve of each of the detectors involved is a calibration curve specific to the detector in question and reflecting the light receiving angle thereof.

In FIG. 6, the vertical axis represents the quantity of light and the horizontal axis denotes the concentration of the target substance. Solid circles stand for the transmitted light detected by the detector 44, triangles represent the scattered light detected by the detector 45A at $\alpha°$, and rectangles denote the scattered light detected by the detector 45B at $\beta°$.

The calibration curves above are used to measure unknown concentrations quantitatively. For the actual measurement, an optimal light receiving angle is determined beforehand in view of the sensitivity and repeatability based on the composition of the reagent in use. Light quantity data from the detector at that light receiving angle is used to perform quantitative measurement.

However, although the other light receiving angles are not optimal for quantitative measurement, they may be used for such measurement in a predetermined dispersion range. The data from these angles may then be used by the embodiment of the present invention in the checks for measurement value abnormalities.

Also, each of the calibration curves is used after a quantifiable range is determined within the limit of determination on the side of lower concentration prescribed by the dispersion range of CV<20% or less and within the limit of determination on the side of higher concentration constrained by the prozone phenomenon and the like.

Thus the checks for measurement value abnormalities are made possible by the embodiment of the present invention within a range where the quantifiable ranges of the detectors 44, 45A and 45B overlap with one another.

Figure 7:
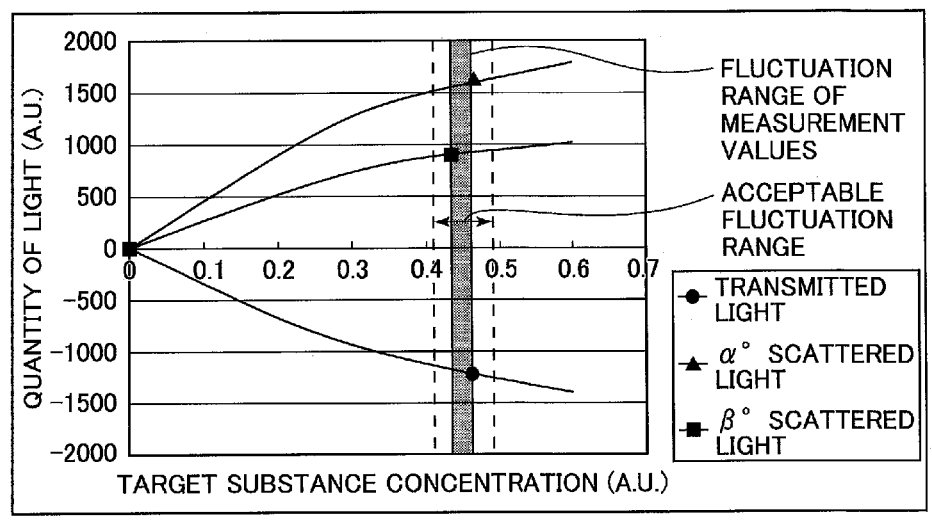
FIG. 7 is a graph showing typical dispersion of normal results of measurement by the embodiment of the present invention.

FIG. 7 is a graph showing typical dispersion of normal results of measurement by the embodiment of the present invention. Broken lines indicate an acceptable fluctuation range. If each of the results of measurement falls within the quantifiable range of the applicable calibration curve, then each result of measurement falls within its acceptable fluctuation range. In the example of FIG. 7, checks are performed using the transmitted light measured at $0°$, the scatted light at $\alpha°$, and the scattered light at $\beta°$. Since the measurement with transmitted light differs significantly from the measurement with scattered light in terms of sensitivity and quantifiable range, only the results of the measurement with scattered light may be used for checks. Similar checks are also possible using multiple absorptiometers at different light projecting positions relative to the reaction cell.

Figure 8:
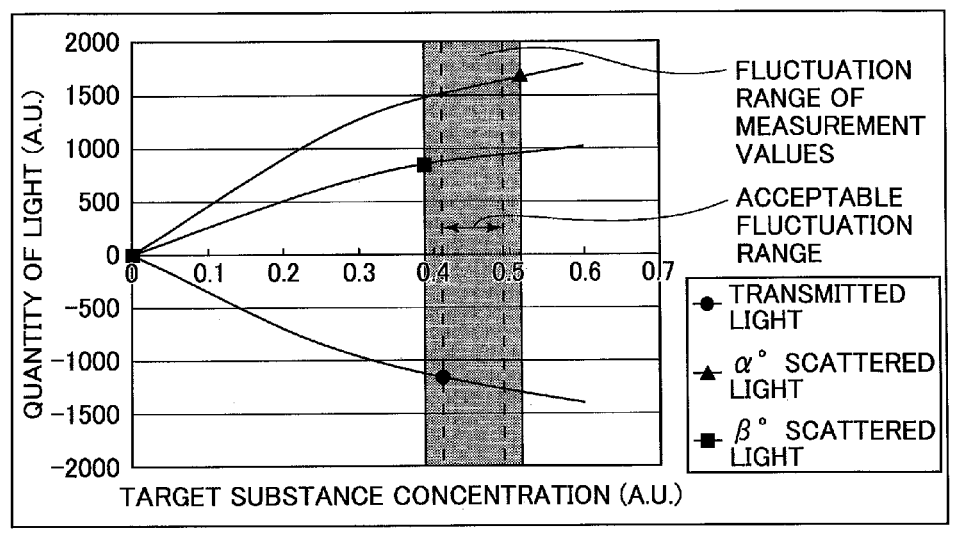
FIG. 8 is a graph showing typical dispersion of abnormal results of measurement by the embodiment of the present invention.

FIG. 8 is a graph showing typical dispersion of abnormal results of measurement by the embodiment of the present invention. In the event of the sudden fluctuation (1) described above at a single point of measurement, the sudden fluctuations (2) above at multiple points of measurement, or the gradual fluctuations (3) above throughout the entire reaction process, there are two resulting cases: one in which the results of measurement at all light receiving angles are affected, and another case in which the results of measurement only at one light receiving angle are affected. In any case, if different detectors at different light receiving angles have different sensitivity levels regarding bubbles or foreign matter, or if different optical systems are in use, the results of measurement in the abnormal state fluctuate more than in the normal state.

As a result, if the fluctuation range of the results of measurement becomes larger than a predetermined default fluctuation range, it can be identified as indicative of an abnormal reaction. At this point, if the results of measurement at different light receiving angles fluctuate similarly due to the presence of bubbles or foreign matter, the fluctuation range is small despite the occurrence of the abnormality. Then the abnormal reaction cannot be expected to be detected.

However, the possibility is very low that the results of measurement at different light receiving angles might fluctuate similarly because of the presence of bubbles or foreign matter. If the default fluctuation range is suitably established, abnormal reactions can be determined unfailingly.

Figure 9:
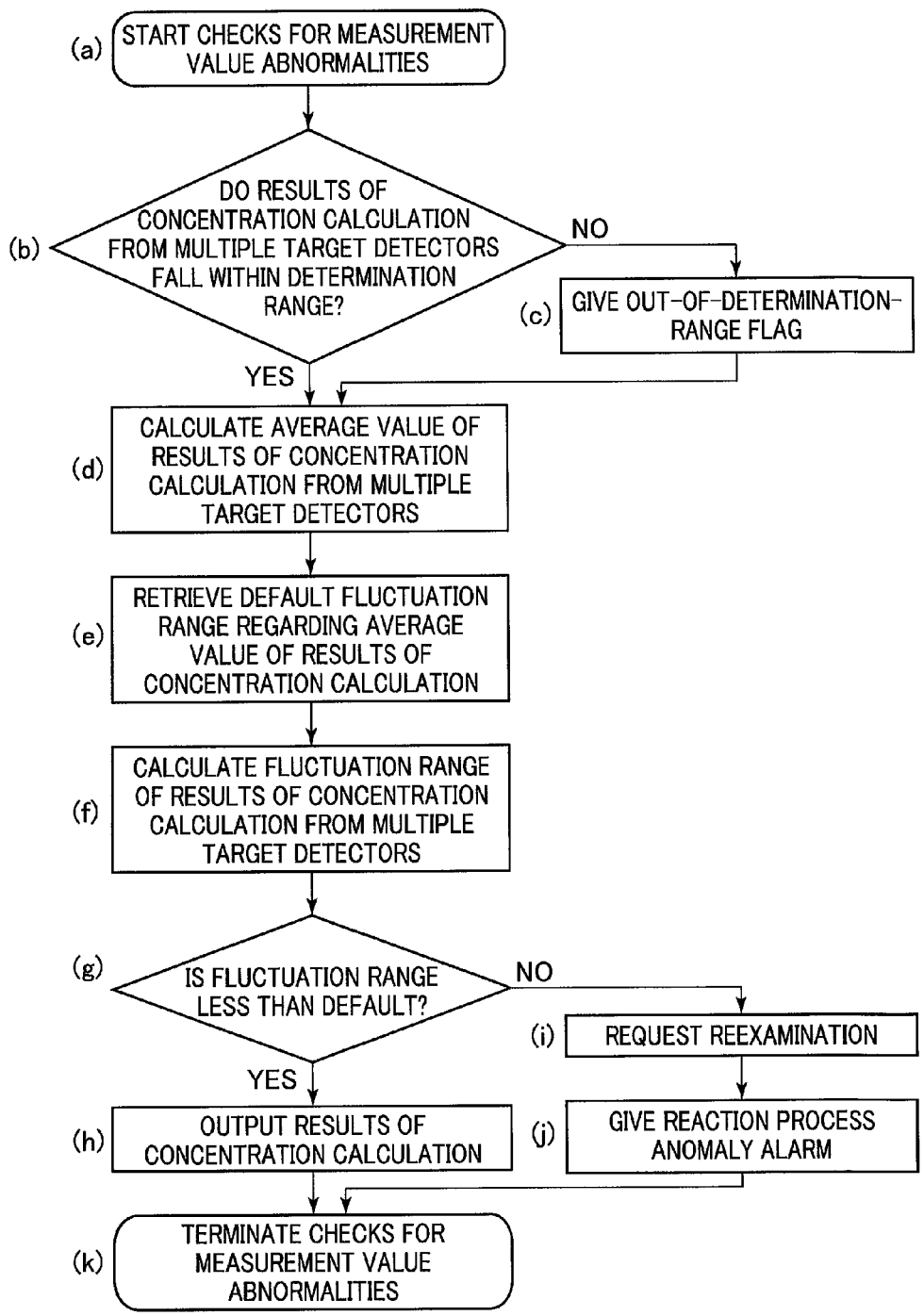
FIG. 9 is an operation flowchart of checks for measurement value abnormalities performed by the automatic analyzer as the embodiment of the present invention.
Figures 10, 11:
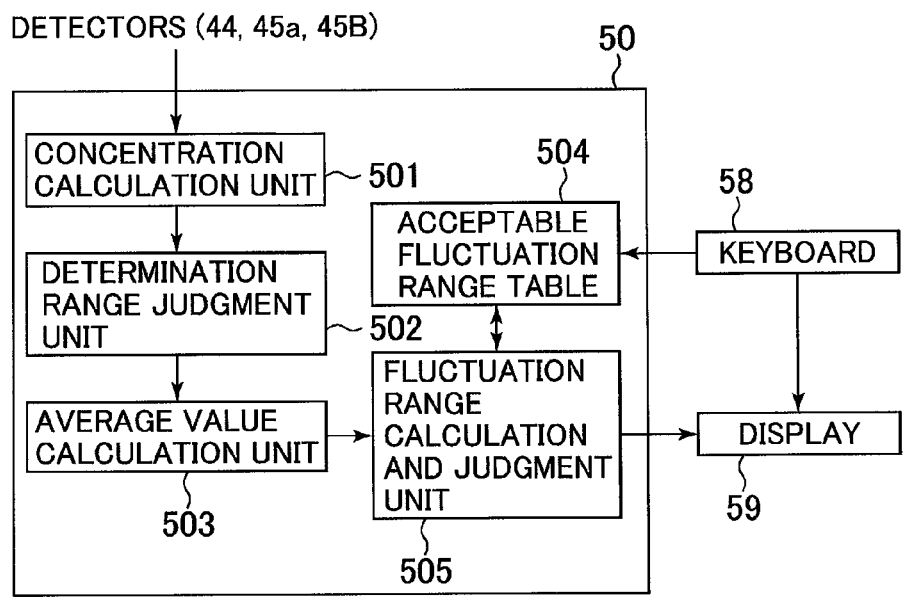
FIG. 10 is a functional block diagram for checking measurement value abnormalities.
FIG. 11 is a schematic diagram showing a typical screen through which default fluctuation ranges are input to check measurement value abnormalities with the embodiment of the present invention.

FIG. 9 is an operation flowchart of checks for measurement value abnormalities performed by the automatic analyzer as the embodiment of the present invention. FIG. 10 is a functional block diagram for checking measurement value abnormalities with the computer 50. In FIG. 10, the computer 50 includes a concentration calculation unit 501 that calculates concentrations based on the detection signals from the detectors 44, 45A and 45B; a determination range judgment unit 502; an average value calculation unit 503; an acceptable fluctuation range table 504; and a fluctuation range calculation and judgment unit 505.

The operation shown in FIG. 9 is performed automatically after the results of measurement are obtained through the analysis operation carried out by the automatic analyzer indicated in FIG. 1.

In FIGS. 9 and 10, when the checks for measurement value abnormalities are started (step (a)), the determination range judgment unit 502 checks to judge whether the results of concentration calculation based on the light quantity data from the multiple target detectors each fall within an applicable determination range (step (b)).

If in step (b) the results of concentration calculation are found to fall within the determination range, the average value calculation unit 503 simply calculates an average value of the results of concentration calculation with the target detectors (step (d)).

If in step (b) the results of concentration calculation are found to fall outside the determination range, the determination range judgment unit 502 gives an out-of-determination-range flag (step (c)). Thereafter, the average value calculation unit 503 calculates the average value of the results of concentration calculation with the target detectors (step (d)). Since the measurement values can provide a clinical material for determination even if they are outside the determination range, the flag is given here, and the checks for measurement value abnormalities are continued.

The fluctuation range calculation and judgment unit 505 retrieves from the acceptable fluctuation range table 504 a default fluctuation range regarding the average value calculated by the average value calculation unit 503 from the results of concentration calculation (step (e)), and calculates accordingly the fluctuation range of the results of concentration calculation with the multiple target detectors (step (f)). The fluctuation range calculation and judgment unit 505 judges whether the calculated fluctuation range falls within the default fluctuation range (step (g)).

If in step (g) the fluctuation range is found to fall within the default range, the fluctuation range calculation and judgment unit 505 outputs the results of concentration calculation to the display 59 (step (h)), and the checks for measurement value abnormalities are terminated (step (k)).

If in step (g) the fluctuation range is found to fall outside the default range, the fluctuation range calculation and judgment unit 505 causes the display 59 to display a reexamination request and add a measurement value abnormality alarm thereto (step (j)). The checks for measurement value abnormalities are then terminated (step (k)).

FIG. 11 is a schematic diagram showing a typical screen through which default fluctuation ranges are input to check measurement value abnormalities with the embodiment of the present invention.

The default fluctuation ranges are stored into the acceptable fluctuation range table 504 by operation of the keyboard 58. The input screen shown in FIG. 11 is displayed on the display 59.

In FIG. 11, the acceptable fluctuation range is set for each item name. It is also possible to set the acceptable fluctuation range for each of different concentration ranges. That is, if the average value of measured concentrations is within a range of 0.01 to 0.1 mg/dL, the acceptable fluctuation range is 0.01 mg/dL. If the average value of measured concentrations is within a range of 0.1 to 1.0 mg/dL, then the acceptable fluctuation range is 0.1 mg/dL.

The same default range may be set for all concentration regions. For the region of high concentrations where the fluctuation range is known to be extensive, different default fluctuation ranges may be set for different concentrations. In this case, the default fluctuation range for a specific concentration range may be determined to be used based on the average value of the measurement values. Alternatively, the default fluctuation range may be determined using a maximum or a minimum value of the results of measurement. Where the minimum measurement value is used, the sensitivity of the checks is higher than if the average value is used. Where the maximum measurement value is used, the sensitivity of the checks becomes lower than if the average value is used. Whereas it is conceivable that the default fluctuation range is set as an eigenvalue for analysis items, the default fluctuation range may also be determined from the fluctuation ranges of multiple data at different concentrations during the preparation of a calibration curve for each of the detectors involved. Such default values can be input not only manually but also automatically on the side of the analyzer.

As another alternative, default value information may be embedded in a barcode for each measurement item, and the barcode may be read by the analyzer.

Where the default range is set for each item to be measured, the accuracy of the checks is improved. Alternatively, the same default range may be determined regardless of the measurement items.

Figure 12:
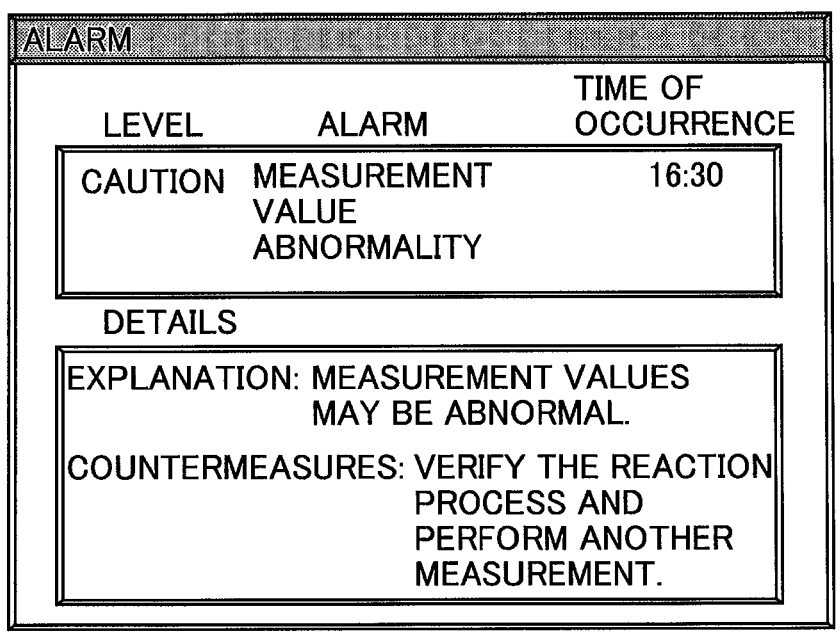
FIG. 12 is a diagram showing a typical measurement value abnormality alarm display screen given by the embodiment of the present invention.

FIG. 12 is a diagram showing a typical measurement value abnormality alarm display screen given by the embodiment of the present invention. The measurement value abnormality alarm display screen on the display 59 indicates an abnormality level, an alarm description of the nature of the abnormality, the time of occurrence, and details (explanation and countermeasures).

If an abnormality is detected through the checks for measurement value abnormalities, the cause of the detected abnormality may be estimated by comparing reaction processes. Also, the analyzer may be arranged to determine the cause automatically.

According to one embodiment of the present invention, as described above, it is possible to provide an automatic analyzer and a method for detecting measurement value abnormalities stemming from reaction process anomalies caused by the presence of foreign matter or bubbles without recourse to complicated processing or functionality of the analyzer.

Whereas the above embodiment has been shown to determine automatically the occurrence of a detection value abnormality and to give the display to that effect, it is also possible to display on the screen the acceptable fluctuation range and the fluctuation range of actual measurement values so that the operator or other personnel may visually determine whether measurement value abnormalities have occurred.

DESCRIPTION OF REFERENCE CHARACTERS

1: Automatic analyzer
10: Reaction disk
11: Reaction cell
12: Thermostatic bath
13: Constant temperature unit
20: Sample disk
21: Sample container
22: Sample pipetting mechanism
23: Movable arm
24: Pipette nozzle
30a: Reagent disk
30b: Reagent disk 31a: Reagent cooling box
31b: Reagent cooling box
32a: Reagent bottle
32b: Reagent bottle
33a: Barcode reader
33b: Barcode reader
34a: Reagent pipetting mechanism
34b: Reagent pipetting mechanism
35a: Stirring mechanism
35b: Stirring mechanism
36: Reaction cell washing mechanism
40: Light source
41: Light scattering photometer
42: Light projecting window
43: Light receiving window
44: Transmitted light detector
45a: α° scattered light detector
45b: β° scattered light detector
46: Light source holder (base component to which the light source is attached)
47: Detector holder (base component to which the detectors are attached)
48: Photometer base
49: Mechanism base
50: Computer
51: Interface
52: Sample pipetting control unit
53: Reagent pipetting control unit
45: A/D converter
55: Printer
56: Memory
57: External output media
58: Keyboard
59: CRT display (display device)
501: Concentration calculation unit
502: Determination range judgment unit
503: Average value calculation unit
504: Acceptable fluctuation range table
505: Fluctuation range calculation and judgment unit

The invention claimed is:

1. An automatic analyzer for analyzing a sample, comprising:
a reagent container storage which stores reagent containers;
a reaction cell storage which stores a reaction cell;
a reagent pipette which pipettes a reagent from the reagent container to the reaction cell;
a sample pipette which pipettes the sample into the reaction cell;
a light source which emits light to illuminate the reaction cell containing a liquid mixture of the sample and the reagent;
a plurality of light intensity detectors including at least first and second light intensity detectors which are disposed to detect the light from the same sample in the reaction cell;
a memory which stores calibration curves for each of the plurality of light intensity detectors, the calibration curves being used to perform quantitative measurement of the same sample;
a display unit which displays analysis results of the same sample in the reaction cell; and
a computer which is connected with the reagent container storage, the reaction cell storage, the reagent pipette, the sample pipette, the plurality of light intensity detectors, and the display unit, wherein the computer is programmed to:
obtain a plurality of detection values, including at least first and second detection values, of the light from the same sample in the reaction cell detected by the light intensity detectors, where the first detection value is detected by the first light intensity detector and the second detection value is detected by the second light intensity detector,
calculate a plurality of concentrations of the same sample in the reaction cell from the detection values, the concentrations including at least a first concentration and a second concentration of the same sample in the reaction cell using the first and second detection values based on a first calibration curve for the first light intensity detector and a second calibration curve for the second light intensity detector from the calibration curves stored in the memory,
obtain a fluctuation range by calculating a difference between the first concentration and the second concentration,
determine whether or not the obtained fluctuation range falls within a predetermined acceptable fluctuation range, and
control the display unit to display an indication that a reaction process abnormality has occurred when the obtained fluctuation range falls outside the predetermined acceptable fluctuation range,
wherein the predetermined acceptable fluctuation range is set according to the calculated concentrations of the same sample in the reaction cell.

2. The automatic analyzer according to claim 1, wherein one of the light intensity detectors is disposed to detect transmitted light from a target substance in the same sample in the reaction cell and another one of the light intensity detectors is disposed to detect scattered light from the target substance in the same sample in the reaction cell.

3. The automatic analyzer according to claim 2, wherein the computer is further programmed to:
calculate an average value of the concentrations calculated from the detection values detected by the light intensity detectors, and
set the predetermined acceptable fluctuation range according to the calculated average value.

4. The automatic analyzer according to claim 2, wherein the computer is further programmed to:
set the predetermined acceptable fluctuation range according to a minimum value of the concentrations calculated from the detection values obtained by the light intensity detectors.

5. The automatic analyzer according to claim 2, wherein the computer is further programmed to:
set the predetermined acceptable fluctuation according to a maximum value of the concentrations calculated from the detection values obtained by the light intensity detectors.

6. A method for detecting measurement value abnormalities of an automatic analyzer which analyzes a sample, the method comprising:
illuminating a reaction cell containing a liquid mixture of the sample and a reagent with light from a light source;
obtaining a plurality of detection values, including at least first and second detection values, of the light from the same sample in the reaction cell which is detected by a plurality of light intensity detectors, including at least first and second light intensity detectors, where the first detection value is detected by the first light intensity detector and the second detection value is detected by the second light intensity detector;

calculating a plurality of concentrations of the same sample in the reaction cell from the detection values, the concentrations including at least a first concentration and a second concentration of the same sample in the reaction cell using the first and second detection values based on a first calibration curve for the first light intensity detector and a second calibration curve for the second light intensity detector;

obtaining a fluctuation range by calculating a difference between the first concentration and the second concentration;

determining whether or not the obtained fluctuation range falls within a predetermined acceptable fluctuation range; and displaying an indication that a reaction process abnormality has occurred when the obtained fluctuation range falls outside the predetermined acceptable fluctuation range, wherein the predetermined acceptable fluctuation range is set according to the calculated concentrations of the same sample in the reaction cell.

7. The method according to claim 6, wherein one of the light intensity detectors detects transmitted light from a target substance in the same sample in the reaction cell and another one of the light intensity detectors detects scattered light from the target substance in the same sample in the reaction cell.

8. The method according to claim 7, further comprising:
calculating an average value of the concentrations from the detection values detected by the light intensity detectors; and
setting the predetermined acceptable fluctuation range according to the calculated average value.

9. The method according to claim 7, further comprising:
setting the predetermined acceptable fluctuation range according to a minimum value of the concentrations calculated from the detection values obtained by the light intensity detectors.

10. The method according to claim 7, further comprising:
setting the predetermined acceptable fluctuation range according to a maximum value of the concentrations calculated from the detection values obtained by the light intensity detectors.

11. The automatic analyzer according to claim 2, wherein each of the first and second light intensity detectors detects scattered light from the target substance.

12. The automatic analyzer according to claim 2, wherein the plurality of light intensity detectors further includes a third light intensity detector which detects scattered light from the target substance.

13. An automatic analyzer for analyzing a sample, comprising:

a reagent container storage which stores reagent containers;

a reaction cell storage which stores a reaction cell;

a reagent pipette which pipettes a reagent from the reagent container to the reaction cell;

a sample pipette which pipettes the sample into the reaction cell;

a light source which emits light to illuminate the reaction cell containing a liquid mixture of the sample and the reagent;

a plurality of light intensity detectors including at least first and second light intensity detectors which are disposed to detect the light from the same sample in the reaction cell;

a memory which stores calibration curves for each of the plurality of light intensity detectors, the calibration curves being used to perform quantitative measurement of the same sample;

a display unit which displays analysis results of the same sample in the reaction cell; and a computer which is connected with the reagent container storage, the reaction cell storage, the reagent pipette, the sample pipette, the plurality of light intensity detectors, and the display unit, wherein the computer is programmed to:
obtain a plurality of detection values, including at least first and second detection values, of the light from the same sample in the reaction cell detected by the light intensity detectors, where the first detection value is detected by the first light intensity detector and the second detection value is detected by the second light intensity detector, calculate a plurality of concentrations of the same sample in the reaction cell from the detection values, the concentrations including at least a first concentration and a second concentration of the same sample in the reaction cell using the first and second detection values based on a first calibration curve for the first light intensity detector and a second calibration curve for the second light intensity detector from the calibration curves stored in the memory, obtain a fluctuation range by calculating a difference between the first concentration and the second concentration, determine whether or not the obtained fluctuation range falls within a predetermined acceptable fluctuation range, and control the display unit to display an indication that a reaction process abnormality has occurred when the obtained fluctuation range falls outside the predetermined acceptable fluctuation range.

* * * * *